: US 12,280,035 B2
(45) Date of Patent: Apr. 22, 2025

(12) United States Patent
Kooijman et al.

(54) CONJUGATED DEOXYNIVALENOL TO PROTECT AGAINST MYCOTOXICOSIS

(71) Applicant: Intervet Inc., Rahway, NJ (US)

(72) Inventors: Sietske Kooijman, Huissen (NL); Rudd Philip Antoon Maria Segers, Boxmeer (NL); Mateusz Walczak, Ottersum (NL); Gudrun Koch, Vienna (AT); Maarten Hendrik Witlvliet, Oostrum (NL)

(73) Assignee: INTERVET INC., Rahway, NJ (US)

( * ) Notice: Subject to any disclaimer, the term of this patent is extended or adjusted under 35 U.S.C. 154(b) by 562 days.

(21) Appl. No.: 17/619,350

(22) PCT Filed: Jul. 2, 2020

(86) PCT No.: PCT/EP2020/068599
§ 371 (c)(1),
(2) Date: Dec. 15, 2021

(87) PCT Pub. No.: WO2021/001462
PCT Pub. Date: Jan. 7, 2021

(65) Prior Publication Data
US 2022/0233496 A1 Jul. 28, 2022

(30) Foreign Application Priority Data
Jul. 3, 2019 (EP) .................................... 19184132

(51) Int. Cl.
A61K 31/352 (2006.01)
A61K 47/64 (2017.01)

(52) U.S. Cl.
CPC .......... A61K 31/352 (2013.01); A61K 47/643 (2017.08)

(58) Field of Classification Search
None
See application file for complete search history.

(56) References Cited

U.S. PATENT DOCUMENTS

2009/0081808 A1  3/2009  Burmeister et al.
2018/0235255 A1  8/2018  Aleschko et al.

FOREIGN PATENT DOCUMENTS

| CN | 101413954 A | 4/2009 |
| CN | 102071169 A | 5/2011 |
| CN | 104693304 A | 6/2015 |
| JP | 2018506993 A | 3/2018 |
| KR | 10-2012-0024239 A | 3/2012 |
| KR | 101270710 B1 | 6/2013 |
| WO | 2007079893 A1 | 7/2007 |
| WO | 2010103017 A2 | 9/2010 |
| WO | WO 2016134387 A1 | 3/2018 |

OTHER PUBLICATIONS

Maragos and McCormick (Food Agricultural Immunol., 12:3, 181-192, 2000).*
Pichler et al (Mycotoxin Res. Jun. 2001: 17 Suppl 2:202-5).*
Eto et al (Brazilian J. Poultry Sci., 14:63-66, 2012).*
Fang, Ji et al., Preparation of deoxynivalenol (DON) artificial antigen and polyclonal antibody, Jiangsu Agricultural Journal, 24(4), 419-424, 2008, abstract only.
Ovchinnikov R.S., et al., Mycotoxins and Mycotoxicoses of Animals as an Actual Problem of Agriculture, гигиены и экологии, 1(25), 114-123, https://elibrary.ru/item.asp?id=36578940, 2018, abstract only.
Zhang, Y et al., Preparation of artificial antigen and polyclonal antibody of deoxynivalenol, Food and Machinery, 26(2), 36-39, 2010, abstract only.
Giovati, et al., Anaflatoxin B1 as the Paradigm of a New Class of Vaccines Based on "Mycotoxoids", Annals of Vaccines and Immunization, 2015, 1010-1017, 2(1).
Zhang, Xiya et al., One-Step Core/Multishell Quantum Dots-Based Fluoroimmunoassay for Screening of Deoxynivalenol in Maize, Food Analytical Methods, 2018, 2569-2578, 11(9).

* cited by examiner

Primary Examiner — Brian Gangle
(74) Attorney, Agent, or Firm — JONES DAY

(57) ABSTRACT

The present invention pertains to the use of conjugated deoxynivalenol (DON) in a method to protect an animal against DON induced mycotoxicosis, in particular to protect against a decrease in average daily weight gain, liver damage, stomach ulcers and/or kidney damage as a result of the ingestion of DON.

12 Claims, No Drawings

CONJUGATED DEOXYNIVALENOL TO PROTECT AGAINST MYCOTOXICOSIS

CROSS-REFERENCE TO RELATED APPLICATIONS

This application is a National Stage entry under 35 U.S.C. § 371 of PCT/EP2020/068599, filed on Jul. 2, 2020, which claims priority to EP Application 19184132.9, filed on Jul. 3, 2019, the content of PCT/EP2020/068599 is hereby incorporated by reference in its entirety.

GENERAL FIELD OF THE INVENTION

The invention in general pertains to protection against mycotoxicosis induced by the mycotoxin deoxynivalenol (DON), also known as vomitoxin. DON is a type B trichothecene which is present predominantly in grains such as wheat, barley, oats, rye, and corn, but also in rice, sorghum, and triticale. The occurrence of deoxynivalenol is associated primarily with *Fusarium graminearum* (*Gibberella zeae*) and *Fusarium culmorum*, both of which are important plant pathogens which cause *fusarium* head blight in wheat and *gibberella* or *fusarium* ear blight in corn. A direct relationship between the incidence of *fusarium* head blight and contamination of wheat with deoxynivalenol has been established. The incidence of *fusarium* head blight is strongly associated with moisture at the time of flowering, and the timing of rainfall, rather than the amount, is the most critical factor. Furthermore, DON contents are significantly affected by the susceptibility of cultivars towards *Fusarium* species, previous crop, tillage practices, and fungicide use. *Fusarium graminearum* grows optimally at a temperature of 25° C., whereas *Fusarium culmorum* grows optimally at 21° C. *Fusarium graminearum* therefore being the more common species occurring in warmer climates.

DON has been implicated in incidents of mycotoxicoses in both humans and farm animals. The toxin belongs to the class of trichothecenes which are strong inhibitors of protein synthesis. Exposure to DON causes the brain to decrease its uptake of the amino acid tryptophan and, in turn, its synthesis of serotonin. Reduced levels of serotonin are believed to be responsible for the anorexic effects of DON. Irritation of the gastrointestinal tract may also play a role in reducing feed intake, and may also partially explain the high incidence of paraesophageal stomach ulcers observed in sows during feed refusal.

Prophylactic treatment of DON induced mycotoxicosis is currently restricted to good agricultural practice to reduce mycotoxins production on crop and control programs of food and feed commodities to ensure that mycotoxin levels remain below certain limits.

BACKGROUND OF THE INVENTION

Fungi cause a broad range of diseases in animals, involving parasitism of organs and tissues as well as allergenic manifestations. However, other than poisoning through ingestion of non-edible mushrooms, fungi can produce mycotoxins and organic chemicals that are responsible for various toxic effects referred to as mycotoxicosis. This disease is caused by exposure to mycotoxins, pharmacologically active compounds produced by filamentous fungi contaminating foodstuffs or animal feeds. Mycotoxins are secondary metabolites not critical to fungal physiology, that are extremely toxic in minimum concentrations to vertebrates upon ingestion, inhalation or skin contact. About 400 mycotoxins are currently recognized, subdivided in families of chemically related molecules with similar biological and structural properties. Of these, approximately a dozen groups regularly receive attention as threats to animal health. Examples of mycotoxins of greatest public interest and agroeconomic significance include aflatoxins (AF), ochratoxins (OT), trichothecenes (T; including DON), zearalenone (ZEN), fumonisins (F), tremorgenic toxins, and ergot alkaloids. Mycotoxins have been related to acute and chronic diseases, with biological effects that vary mainly according to the diversity in their chemical structure, but also with regard to biological, nutritional and environmental factors. The pathophysiology of mycotoxicoses is the consequence of interactions of mycotoxins with functional molecules and organelles in the animal cell, which may result in carcinogenicity, genotoxicity, inhibition of protein synthesis, immunosuppression, dermal irritation, and other metabolic perturbations. In sensitive animal species, mycotoxins may elicit complicated and overlapping toxic effects. Mycotoxicoses are not contagious, nor is there significant stimulation of the immune system. Treatment with drugs or antibiotics has little or no effect on the course of the disease. To date no human or animal vaccine is available for combating mycotoxicoses.

A growing body of work is thus focusing in developing vaccines and/or immunotherapy with efficacy against broad fungal classes as a powerful tool in combating mycoses, i.e. the infection with the fungi as such, instead of the toxins, in the prevention of specific fungal diseases. In contrast to mycoses, mycotoxicoses do not need the involvement of the toxin producing fungus and are considered as abiotic hazards, although with biotic origin. In this sense, mycotoxicoses have been considered examples of poisoning by natural means, and protective strategies have essentially focused on exposure prevention. Human and animal exposure occurs mainly from ingestion of the mycotoxins in plant-based food. Metabolism of ingested mycotoxins could result in accumulation in different organs or tissues; mycotoxins can thus enter into the food chain through animal meat, milk, or eggs (carry over). Because toxigenic fungi contaminate several kinds of crops for human and animal consumption, mycotoxins may be present in all kinds of raw agricultural materials, commodities and beverages. The Food and Agriculture Organization (FAO) estimated that 25% of the world's food crops are significantly contaminated with mycotoxins. At the moment, the best strategies for mycotoxicoses prevention include good agricultural practice to reduce mycotoxins production on crop and control programs of food and feed commodities to ensure that mycotoxin levels stand below predetermined threshold limits. These strategies may limit the problem of contamination of commodities with some groups of mycotoxins with high costs and variable effectiveness. Except for supportive therapy (e.g., diet, hydration), there are almost no treatments for mycotoxin exposure and antidotes for mycotoxins are generally not available, although in individual exposed to AFs some encouraging results have been obtained with some protective agents such as chlorophyllin, green tea polyphenols and dithiolethiones (oltipraz).

Vaccination against particular mycotoxins has been proposed to prevent mycotoxicosis in livestock and contamination by mycotoxins in important foods of animal origin with a strategy based on the production of antibodies that could specifically block initial absorption or bioactivation of mycotoxins, their toxicity and/or secretion in animal products (such as milk) by immuno-interception.

The production of vaccines for protection against mycotoxicoses however are very challenging, principally related to the wide range of structures, chemical properties, and toxicity associated with mycotoxins. Mycotoxins are low molecular weight, usually nonproteinaceous molecules, which are not ordinarily immunogenic (haptens), but can potentially elicit an immune response when attached to a large carrier molecule such as a protein. Methods for conjugation of mycotoxins to protein or polypeptide carrier and optimization of conditions for animal immunization have been extensively studied, with the purpose of producing monoclonal or polyclonal antibodies with different specificities to be used in immunoassay for screening of mycotoxins in products destined for animal and human consumption. Coupling proteins used in these studies included bovine serum albumin (BSA), keyhole limpet haemocyanin (KLH), thyroglobulin (TG) and polylysine, among others. In the past decades, many efforts have been made for developing mycotoxin derivatives that can be bound to proteins while retaining enough of the original structure so that antibodies produced will recognize the native toxin. Through these methods, antibodies against many mycotoxins have been made available, demonstrating that conjugation to proteins may be an effective tool for immunization. The application of this strategy for human and animal vaccination, thus to arrive at protection while being safe for the recipient, has not been successful so far due to the toxic properties of the molecules that might be released in vivo. For example, conjugation of toxins such as T-2 to protein carriers has been shown to result in unstable complexes with potential release of the free toxin in its active form (Chanh et al, *Monoclonal anti-idiotype induces protection against the cytotoxicity of the trichothecene mycotoxin T-2*, in J Immunol. 1990, 144: 4721-4728). In analogy with toxoid vaccines, which may confer a state of protection against the pathological effects of bacterial toxins, a reasonable approach to the development of vaccines against mycotoxin may be based on conjugated "mycotoxoids", defined as modified form of mycotoxins, devoid of toxicity although maintaining antigenicity (Giovati L et al, *Anaflatoxin B1 as the paradigm of a new class of vaccines based on "Mycotoxoids"*, in Ann Vaccines Immunization 2(1): 1010, 2015). Given the nonproteinaceous nature of mycotoxins, the approach for conversion to mycotoxoids should rely on chemical derivatization. The introduction of specific groups in strategic positions of the related parent mycotoxin may lead to formation of molecules with different physicochemical characteristics, but still able to induce antibodies with sufficient cross-reacting to the native toxin. The common rationale for mycotoxin vaccination would thus be based on generating antibodies against the mycotoxoid with an enhanced ability to bind native mycotoxin compared with cellular targets, neutralizing the toxin and preventing disease development in the event of exposure. A potential application of this strategy has been demonstrated in the case of mycotoxins belonging to the AF group (Giovati et al, 2015), but not for any of the other mycotoxins. Moreover, the protective effect has not been demonstrated against mycotoxicosis of the vaccinated animal as such, but only against carry over in dairy cows to their milk, so as to protect people that consume the milk or products made thereof from mycotoxicosis.

OBJECT OF THE INVENTION

It is an object of the invention to provide a method to protect an animal against mycotoxicosis induced by deoxynivalenol, one of the most widely spread mycotoxins in animal feed.

SUMMARY OF THE INVENTION

In order to meet the object of the invention it has been found that conjugated deoxynivalenol (DON) is suitable for use in a method to protect an animal against DON induced mycotoxicosis. It was found that there was no need to convert the DON into a toxoid, the conjugated toxin appeared to be safe for the treated host animal. Also, it was surprising to see that the immune response induced was strong enough to protect the animal itself against mycotoxicosis after ingestion of DON post treatment. Such actual protection by inducing an immune response against the mycotoxin itself has not been shown in the art for any mycotoxin, let alone for the highly abundant and extremely toxic compound deoxynivalenol.

Definitions

Mycotoxicosis is the disease resulting from exposure to a mycotoxin. The clinical signs, target organs, and outcome depend on the intrinsic toxic features of the mycotoxin and the quantity and length of exposure, as well as the health status of the exposed animal.

To protect against mycotoxicosis means to prevent or decrease one or more of the negative physiological effects of the mycotoxin in the animal, such as a decrease in average daily weight gain.

Deoxynivalenol (also known as vomitoxin or VOM) is a mycotoxin produced by the fungus *Fusarium graminearum*, which causes *Fusarium* head blight (FHB), or scab, of small grains. DON can cause feed refusal and vomiting. The molecular formula of the basic compound is $C_{15}H_{20}O_6$.

A conjugated molecule is a molecule to which an immunogenic compound is coupled through a covalent bond. Typically the immunogenic compound is a large protein such as KLH, BSA or OVA.

An adjuvant is non-specific immunostimulating agent. In principal, each substance that is able to favor or amplify a particular process in the cascade of immunological events, ultimately leading to a better immunological response (i.e. the integrated bodily response to an antigen, in particular one mediated by lymphocytes and typically involving recognition of antigens by specific antibodies or previously sensitized lymphocytes), can be defined as an adjuvant. An adjuvant is in general not required for the said particular process to occur, but merely favors or amplifies the said process.

FURTHER EMBODIMENTS OF THE INVENTION

In a further embodiment of the invention, the conjugated DON is systemically administered to the animal. Although local administration, for example via mucosal tissue in the gastro-intestinal tract (oral or anal cavity) or in the eyes (for example when immunising chickens) is known to be an effective route to induce an immune response in various animals, it was found that systemic administration leads to an adequate immune response for protecting animals against a DON induced mycotoxicosis. It was found in particular that effective immunisation can be obtained upon intramuscular, oral and/or intradermal administration.

The age of administration is not critical, although it is preferred that the administration takes place before the animal is able to ingest feed contaminated with substantial amounts of DON. Hence a preferred age at the time of administration of 6 weeks or younger. Further preferred is an age of 4 weeks or younger, such as for example an age of 1-3 weeks.

In yet another embodiment of the invention the conjugated DON is administered to the animal at least twice. Although many animals (in particular swine chickens, ruminants) in general are susceptible for immunisation by only one shot of an immunogenic composition, it is believed that for economic viable protection against DON two shots are preferred. This is because in practice the immune system of the animals will not be triggered to produce anti-DON antibodies by natural exposure to DON, simply because naturally occurring DON is not immunogenic. So, the immune system of the animals is completely dependent on the administration of the conjugated DON. The time between the two shots of the conjugated DON can be anything between 1 week and 1-2 years. For young animals it is believed that a regime of a prime immunisation, for example at 1-3 weeks of age, followed by a booster administration 1-4 weeks later, typically 1-3 weeks later, such as 2 weeks later, will suffice. Older animals may need a booster administration every few months (such as 4, 5, 6 months after the last administration), or on a yearly or biannual basis as is known form other commercially applied immunisation regimes for animals.

In still another embodiment the conjugated DON is used in a composition comprising an adjuvant in addition to the conjugated DON. An adjuvant may be used if the conjugate on itself is not able to induce an immune response to obtain a predetermined level of protection. Although conjugate molecules are known that are able to sufficiently stimulate the immune system without an additional adjuvant, such as KLH or BSA, it may be advantageous to use an additional adjuvant. This could take away the need for a booster administration or prolong the interval for the administration thereof. All depends on the level of protection needed in a specific situation. A type of adjuvant that was shown to be able and induce a good immune response against DON when using conjugated-DON as immunogen is an emulsion of water and oil, such as for example a water-in-oil emulsion or an oil-in-water emulsion. The former is typically used in poultry while the latter is typically used in animals who are more prone to adjuvant induced site reactions such as swine and ruminants.

In again another embodiment the conjugated DON comprises DON conjugated to a protein having a molecular mass above 10,000 Da. Such proteins, in particular keyhole limpet hemocyanin (KLH) and ovalbumin (OVA), have been found to be able and induce an adequate immune response in animals, in particular in swine and chickens. A practical upper limit for the protein might be 100 MDa.

Regarding the protection against mycotoxicosis, it was found in particular that using the invention, the animal is protected against a decrease in average daily weight gain, liver damage, stomach ulcers and/or kidney damage, thus one or more of these signs of mycotoxicosis.

The invention will now be further explained using the following examples.

EXAMPLES OF THE INVENTION

Example 1: Immunisation Challenge Experiment Using Conjugated DON

Objective

The objective of this study was to evaluate the efficacy of conjugated deoxynivalenol to protect an animal against mycotoxicosis due to DON ingestion. To examine this, pigs were immunised twice with DON-KLH before being challenged with toxic DON. Different routes of immunisation were used to study the influence of the route of administration.

Study Design

Fourty 1 week old pigs derived from 8 sows were used in the study, divided over 5 groups. Twenty-four piglets of group 1-3 were immunised twice at 1 and 3 weeks of age. Group 1 was immunised intramuscularly (IM) at both ages. Group 2 received an IM injection at one week of age and an oral boost at three weeks of age. Group 3 was immunised intradermally (ID) two times. From 5½% weeks of age groups 1-3 were challenged during 4 weeks with DON administered orally in a liquid. Group 4 was not immunised but was only challenged with DON as described for groups 1-3. Group 5 served as a control and only received a control fluid, from the age of 5.5 weeks for 4 weeks.

The DON concentration in the liquid formulation corresponded to an amount of 5.4 mg/kg feed. This corresponds to an average amount of 2.5 mg DON per day. After four weeks of challenge all animals were post-mortem investigated, with special attentions for the liver, kidneys and the stomach. In addition, blood sampling was done at day 0, 34, 41, 49, 55, 64 (after euthanasia) of the study, except for group 5 of which blood samples were taken only at day 0, 34, 49, and directly after euthanasia.

Test Articles

Three different immunogenic compositions were formulated, namely Test Article 1 comprising DON-KLH at 50 µg/ml in an oil-in-water emulsion for injection (X-solve 50, MSD AH, Boxmeer) which was used for IM immunization; Test Article 2 comprising DON-KLH at 50 µg/ml in a water-in-oil emulsion (GNE, MSD AH, Boxmeer) which was used for oral immunization and Test Article 3 comprising DON-KLH at 500 µg/ml in an oil-in-water emulsion for injection (X-solve 50) for ID immunisation.

The challenge deoxynivalenol (obtained from Fermentek, Israel) was diluted in 100% methanol at a final concentration of 100 mg/ml and stored at <−15° C. Prior to usage, DON was further diluted and supplied in a treat for administration.

Inclusion Criteria

Only healthy animals were used. In order to exclude unhealthy animals, all animals were examined before the start of the study for their general physical appearance and absence of clinical abnormalities or disease. Per group piglets from different sows were used. In everyday practice all animals will be immunised even when pre-exposed to DON via intake of DON contaminated feed. Since DON as such does not raise an immune response, it is believed that there is no principle difference between animals pre-exposed to DON and naïve with respect to DON.

Results

None of the animals had negative effects associated with the immunisation with DON-KLH. The composition thus appeared to be safe.

All pigs were serologically negative for titres against DON at the start of the experiment, During the challenge the groups immunised intramuscular (Group 1) and intradermally (Group 3) developed antibody responses against DON as measured by ELISA with native DON-BSA as the coating antigen. Table 1 depicts the average IgG values on 4 time points during the study with their SD values. Both Intramuscular immunisation and Intradermal immunisation induced significant titres against DON.

TABLE 1

IgG titres

|  | group 1 | group 2 | group 3 | group 4 | Group 5 |
|---|---|---|---|---|---|
| T = 0 | <4.3 | <4.3 | <4.3 | <4.3 | <4.3 |
| T = 35 | 11.2 | 4.86 | 9.99 | 4.3 | 4.19 |
| T = 49 | 9.56 | 4.64 | 8.81 | 4.71 | 3.97 |
| T = 64 | 8.48 | 4.3 | 7.56 | 4.3 | 3.31 |

As depicted in Table 2 all immunised animals, including the animals in Group 2 that showed no significant anti-DON IgG titre increase, showed a significant higher weight gain during the first 15 days compared to the challenge animals. With respect to the challenged animals, all animals gained more weight over the course of the study.

TABLE 2 weight analysis

|  | ADG1[1] | ADG[2] | weight begin | weight end | Average additional weight gain compared to challenge animals (grams) |
|---|---|---|---|---|---|
| group 1 | 0.67 | 0.80 | 11.63 | 32.29 | +1060 |
| group 2 | 0.64 | 0.79 | 12.31 | 32.13 | +760 |
| group 3 | 0.58 | 0.82 | 12.88 | 32.25 | +310 |
| group 4 | 0.54 | 0.81 | 12.69 | 31.75 | 0 |
| group 5 | 0.57 | 0.80 | 11.63 | 31.08 | +390 |

[1]average daily weight gain over the first 15 days of the challenge
[2]average daily weight gain over the last 13 days of the challenge The condition of the small intestines (as determined by the villus/crypt ratio in the jejunum) was also monitored. In table 3 the villus/crypt ratio is depicted. As can be seen, the animals in group 3 had an average villus crypt/crypt ratio comparable to the healthy controls (group 5), while the non-immunised, challenged group (group 4) had a much lower (statistically significant) villus crypt ratio. In addition, group 1 and group 2, had a villus/crypt ratio which was significantly better (i.e. higher) compared to the non-immunised challenge control group. This indicates that the immunisation protects against the damage of the intestine, initiated by DON.

TABLE 3 villus/crypt ratio

|  | group 1 | group 2 | group 3 | group 4 | group 5 |
|---|---|---|---|---|---|
| average | 1.57 | 1.41 | 1.78 | 1.09 | 1.71 |
| STD | 0.24 | 0.22 | 0.12 | 0.10 | 0.23 |

The general condition of other organs was also monitored, more specifically the liver, the kidneys and the stomach. It was observed that all three test groups (groups 1-3) were in better health than the non-immunised challenge control group (group 4). In table 4 a summary of the general health data is depicted. The degree of stomach ulcer is reported from-(no prove of ulcer formation) to ++ (multiple ulcers). The degree of stomach inflammation is reported from-(no prove of inflammation) to ++/- (initiation of stomach inflammation).

TABLE 4

General health data

|  | Liver colour | Stomach ulcer | Stomach inflammation | Kidneys |
|---|---|---|---|---|
| Group 1 | Normal-yellow | – | – | Pail |
| Group 2 | Normal | +/-- | – | Normal |
| Group 3 | Normal | +/- | +/-- | Normal |
| Group 4 | Pail | ++ | ++/- | Pail |
| Group 5 | Normal | + | ++/- | Normal |

Example 2: Effect of Immunisation on DON Levels

Objective

The objective of this study was to evaluate the effects of immunization with a DON conjugate on the toxicokinetics of DON ingestion. To examine this, pigs were immunised twice with DON-KLH before being fed toxic DON.

Study Design

Ten 3 week old pigs were used in the study, divided over 2 groups of 5 pigs each. The pigs in Group 1 were immunised IM twice at 3 and 6 weeks of age with DON-KLH (Test Article 1; example 1). Group 2 served as a control and only received a control fluid. At the age of 11 weeks the animals were each administered DON (Fermentek, Israel) via a bolus at a dose of 0.05 mg/kg which (based on the daily feed intake) resembled a contamination level of 1 mg/kg feed. Blood samples of the pigs were taken juts before DON administration and 0.25, 0.5, 0.75, 1, 1.5, 2, 3, 4, 6, 8, and 12 h post DON administration.

Inclusion Criteria

Only healthy animals were used.

Analysis of DON in Plasma

Plasma analysis of unbound DON was done using a validated LC-MS/MS method on an Acquity® UPLC system coupled to a Xevo® TQ-S MS instrument (Waters, Zellik, Belgium). The lower limit of quantification of DON in pig plasma using this method is 0.1 ng/ml.

Toxicokinetic Analysis

Toxicokinetic modeling of the plasma concentration-time profiles of DON was done by noncompartmental analysis (Phoenix, Pharsight Corporation, USA). Following parameters were calculated: area under the curve from time zero to infinite ($AUC_{0\rightarrow\infty}$), maximal plasma concentration ($C_{max}$), and time at maximal plasma concentration ($t_{max}$).

Results

The toxicokinetic results are indicated in table 5 here beneath. As can be seen immunisation with DON-KLH decreases all toxicokinetic parameters. As it is unbound DON that is responsible for the exertion of toxic effects, it may be concluded that immunisation with DON-KLH will reduce the toxic effects caused by DON by reducing the amount of unbound DON in the blood of animals.

TABLE 5

| Toxicokinetic parameters of unbound DON | | |
|---|---|---|
| Toxicokinetic parameter | DON-KLH | Control |
| $AUC_{0\rightarrow\infty}$ | 77.3 ± 23.6 | 187 ± 33 |
| $C_{max}$ | 12.5 ± 2.7 | 30.8 ± 2.5 |
| $t_{max}$ | 1.69 ± 1.03 | 2.19 ± 1.07 |

Example 3: Serological Response Against Various DON Conjugates

Objective

The objective of this study was to evaluate the efficacy of different conjugated deoxynivalenol products.

Study Design

Eighteen 3 week old pigs were used in the study, divided over 3 groups of six pigs each. The pigs of group 1 were immunised twice intramuscularly at 3 and 5 weeks of age with DON-KLH (using Test Article 1 of Example 1). Group 2 was immunised correspondingly with DON-OVA. Group 3 served as a negative control. All animals were checked for an anti-DON IgG response at 3 weeks of age, 5 weeks of age and 8 weeks of age.

Results

The serological results are indicated here below in the table in log2 antibody titre.

TABLE 6

| anti-DON IgG response | | | |
|---|---|---|---|
| Test Article | 3 weeks | 5 weeks | 8 weeks |
| DON-KLH | 3.5 | 6.6 | 8.3 |
| DON-OVA | 3.3 | 3.9 | 11.8 |
| Control | 4.8 | 3.3 | 3.3 |

It appears that both conjugates are suitable to raise an anti-DON IgG response. Also, a response appears be induced by one shot only.

Example 4: Serological Response in Chickens

Objective

The objective of this study was to evaluate the serological response of DON-KLH in chickens.

Study Design

For this study 30 four week-old chickens were used, divided over three groups of 10 chickens each. The chickens were immunized intramuscularly with DON-KLH. Group 1 was used as a control and received PBS only. Group 2 received DON-KLH without any adjuvant and group 3 received DON-KLH formulated in GNE adjuvant (available from MSD Animal Health, Boxmeer). A prime immunization was given on day 0 with 0.5 ml vaccine into right leg. On day 14, chickens received a comparable booster immunization into the left leg.

Blood sampling took place at day 0 and 14, as well as on day 35, 56, 70 and 84. Serum was isolated for the determination of IgY against DON. At day 0 and 14 blood samples were isolated just before immunisation.

Results

The serological results are depicted in table 7 in log2 antibody titre. The PBS background has been subtracted from the data.

TABLE 7

| anti-DON IgY response | | | | | | |
|---|---|---|---|---|---|---|
| Vaccine | Day 0 | Day 14 | Day 35 | Day 56 | Day 70 | Day 84 |
| DON-KLH | 0 | 0 | 0.6 | 1.2 | 1.1 | 1.2 |
| DON-KLH in GNE | 0 | 1.9 | 6.5 | 6.0 | 6.7 | 7.7 |

As can be seen, the conjugated DON also induces an anti-DON titre in chickens. GNE adjuvant increases the response substantially but appears to be not essential for obtaining a net response as such.

The invention claimed is:

1. A method of protecting an animal against DON (deoxynivalenol) induced mycotoxicosis comprising systemically administering conjugated DON to the animal at an age of 6 weeks or younger.

2. The method of claim 1, wherein the conjugated DON is administered to the animal intramuscularly, orally and/or intradermally.

3. The method of claim 1, wherein the conjugated DON is administered to the animal at an age of 4 weeks or younger.

4. The method of claim 3, wherein the conjugated DON is administered to the animal at an age of 1-3 weeks.

5. The method of claim 1, wherein the conjugated DON is administered to the animal at least twice.

6. The method of claim 1, wherein the conjugated DON is used in a composition comprising an adjuvant in addition to the conjugated DON.

7. The method of claim 6, wherein the adjuvant is an emulsion of water and oil.

8. The method of claim 7, wherein the adjuvant is a water-in-oil emulsion or an oil-in-water emulsion.

9. The method of claim 1, wherein the conjugated DON comprises DON conjugated to a protein having a molecular mass above 10,000 Da.

10. The method of claim 9, wherein the conjugated DON comprises DON conjugated to keyhole limpet hemocyanin (KLH) or ovalbumin (OVA).

11. The method of claim 1, wherein the animal is protected against a decrease in average daily weight gain, liver damage, stomach ulcers and/or kidney damage.

12. The method of claim 1, wherein the animal is a swine or chicken.

* * * * *

UNITED STATES PATENT AND TRADEMARK OFFICE
CERTIFICATE OF CORRECTION

PATENT NO. : 12,280,035 B2  
APPLICATION NO. : 17/619350  
DATED : April 22, 2025  
INVENTOR(S) : Sietske Kooijman et al.

Page 1 of 1

It is certified that error appears in the above-identified patent and that said Letters Patent is hereby corrected as shown below:

On the Title Page

"(72) Inventors: Sietske Kooijman, Huissen (NL); Rudd Philip Antoon Maria Segers, Boxmeer (NL); Mateusz Walczak, Ottersum (NL); Gudrun Koch, Vienna (AT); Maarten Hendrik Witlvliet, Oostrum (NL)"

Should read:
--(72) Inventors: Sietske Kooijman, Huissen (NL); Ruud Philip Antoon Maria Segers, Boxmeer (NL); Mateusz Walczak, Ottersum (NL); Gudrun Koch, Vienna (AT); Maarten Hendrik Witvliet, Oostrum (NL)--

Signed and Sealed this  
Fifteenth Day of July, 2025

Coke Morgan Stewart  
*Acting Director of the United States Patent and Trademark Office*